(12) United States Patent
Ghelmansarai (10) Patent No.: US 7,881,772 B2
(45) Date of Patent: Feb. 1, 2011

(54) ELECTRONIC PORTAL IMAGING FOR RADIOTHERAPY

(75) Inventor: Farhad Abbasi Ghelmansarai, Danville, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1765 days.

(21) Appl. No.: 10/099,583

(22) Filed: Mar. 15, 2002

(65) Prior Publication Data

US 2003/0176779 A1    Sep. 18, 2003

(51) Int. Cl.
*A61B 5/05* (2006.01)
(52) U.S. Cl. ........................ 600/427; 600/407; 378/98.2
(58) Field of Classification Search ................. 600/427; 378/65
See application file for complete search history.

(56) References Cited

U.S. PATENT DOCUMENTS

| 6,300,648 | B1   | 10/2001 | Mei et al. |
| 6,307,915 | B1 * | 10/2001 | Frojdh ........................ 378/98.8 |
| 6,341,172 | B1 * | 1/2002  | Xu et al. ...................... 382/132 |
| 6,487,274 | B2 * | 11/2002 | Bertsche ...................... 378/143 |
| 6,510,202 | B2 * | 1/2003  | Tamura et al. ............... 378/155 |
| 6,842,502 | B2 * | 1/2005  | Jaffray et al. ................. 378/65 |
| 6,925,149 | B2 * | 8/2005  | Ghelmansarai ............ 378/98.2 |

OTHER PUBLICATIONS

RID 1640 AF1 and ALF: "Radiation Image Detectors 1640", Brochures dated May 2001, download from www.perkinelmer.com/opto—2 pgs.

P. Munro—"X-Ray Quantum Limited Portal Imaging Using Amorphous Silicon Flat—Panel Arrays", downloaded from http://www.1rcc.on.ca/research/staff/pmunro/a-Si_paper/a-Si_paper.html, on Feb. 19, 2002, 45 pgs.
Varian: "Oncology Systems: Key Features". Downloaded from http://www.varian.com/onc/upg115a.html, on Feb. 19, 2002.
Donhoe, Gregory W., "Spacecraft Focal Plane Array Readout Correction"., Revision A Jan. 3, 2001—5 pgs.
Graeve, Thorsten and Weckler, Gene P., "High-resolution CMOS imaging Detector", 2001—9 pgs.
R.B. Apte et al., "Large-Area, Low-Noise Amorphous Silicon Imaging System", undated—7 pgs.

* cited by examiner

*Primary Examiner*—Long V Le
*Assistant Examiner*—Ellsworth Weatherby (57) ABSTRACT

Some embodiments include transmission of a pulse to imaging elements in order to read an image frame from the imaging elements, prior to exposure of the imaging elements to radiation that is to be converted to and captured as image data, wherein the pulse is transmitted so that the image frame is read and the imaging elements become ready to capture image data associated with the radiation substantially immediately before the imaging elements are exposed to the radiation. Embodiments may also include transmission of a second pulse to the imaging elements in order to read a second image frame from the imaging elements, wherein the second pulse is transmitted at a predetermined time after the exposure of the imaging elements to the radiation is complete, wherein one of the imaging elements produces second radiation after the exposure of the imaging elements to the radiation is complete, and wherein the predetermined time is a time suitable to substantially capture image data associated with the second radiation.

9 Claims, 7 Drawing Sheets

ELECTRONIC PORTAL IMAGING FOR RADIOTHERAPY

BACKGROUND

1. Field

The present invention relates generally to the reduction of dark current effects on imaging devices, and may be applied, for example, to portal imaging in conjunction with radiation therapy.

2. Description

Many types of conventional imaging devices create and represent image data using stored electrical charge. For example, known charge-coupled devices and amorphous silicon devices convert light to electrical charge and store the electrical charge for subsequent readout. In the case of amorphous silicon devices, a scintillator layer receives x-rays and generates light in proportion to the intensity of the received x-rays. An array of amorphous silicon photodiodes then converts and stores the generated light as electrical charge.

X-ray radiation may also be converted to and stored as electrical charge using amorphous selenium imaging devices. In operation, x-rays are absorbed by an array amorphous selenium photoconductors, which convert the x-rays directly to stored electrical charge. Due to the manner in which they operate, amorphous selenium imaging devices are said to produce image data through direct detection while amorphous silicon imaging devices are said to use indirect detection.

Because they rely on electrical charge to represent image data, the above-described imaging devices, and those that share similar characteristics, are vulnerable to phenomena that could adversely influence the conversion of light or other radiation to electrical charge and/or the storage of the electrical charge. Dark current is one such phenomenon.

For example, a photodiode of an amorphous silicon imaging device accumulates charge in proportion to an intensity of light received from an associated scintillator. After a specified time period, the accumulated charge is read in order to calculate the intensity of an image pixel associated with the photodiode. Accordingly, the accumulated charge is preferably directly proportional to the received light. The photodiode, however, requires a small bias voltage for proper operation. This bias voltage generates a small "dark current" that may cause a charge to accumulate within the photodiode that is unrelated to the intensity of the received light. This dark current thereby causes errors in the calculated intensity of the associated image pixel. Other imaging devices that convert radiation to electrical charge suffer from similar dark current problems.

Several approaches have been taken in an attempt to address the foregoing. According to one approach, imaging devices are designed so as to minimize dark currents and/or the effects thereof. This approach involves the development of new semiconductor devices, doping techniques and circuit designs, and therefore can be quite costly. Moreover, no known technique has been shown to efficiently and satisfactorily address dark current issues.

Another approach applies image processing techniques to each image frame that is produced from electrical charges read from an array of imaging elements. Known as offset correction, this approach involves acquiring image frames during a period of non-irradiation, calculating an average image frame from the acquired frames, and subtracting the average image frame from each frame acquired during subsequent radiation of the imaging elements. The averaged image frames are preferably acquired at a same rate as the subsequently-acquired frames so as to better approximate the effect of dark current on the subsequently-acquired frames. Since the extent of dark current effects vary across imaging devices, imaging devices are often sold with customized software for performing offset correction.

Offset correction often fails to provide suitable reduction of dark current effects, alone or in combination with the first approach described above. Therefore, additional or alternative systems for reducing dark current effects are desirable.

SUMMARY

To address at least the above problems, some embodiments of the present invention provide a system, method, apparatus, and means to transmit, prior to exposure of imaging elements to radiation that is to be converted to and captured as image data, a pulse to the imaging elements in order to read an image frame from the imaging elements, wherein the pulse is transmitted so that the image frame is read and the imaging elements become ready to capture image data associated with the radiation substantially immediately before the imaging elements are exposed to the radiation.

Also according to some embodiments, a second pulse is transmitted to the imaging elements in order to read a second image frame from the imaging elements, wherein the second pulse is transmitted at a predetermined time after the exposure of the imaging elements to the radiation is complete, wherein one of the imaging elements produces second radiation after the exposure of the imaging elements to the radiation is complete, and wherein the predetermined time is a time suitable to substantially capture image data associated with the second radiation.

In some embodiments, the invention operates to transmit a pulse as described above and to detect a linear accelerator pulse, determine if the linear accelerator pulse is detected while the image frame is being read from the imaging elements, transmit, if it is determined that the linear accelerator pulse is not detected while the image frame is being read from the imaging elements, a second pulse to the imaging elements in order to read a second image frame from the imaging elements, determine that the exposure of the imaging elements to the radiation is complete, and transmit a third pulse to the imaging elements in order to read a third image frame from the imaging elements after an immediately-previous image frame is read from the imaging elements.

According to some aspects, the invention may operate to determine whether to operate in a first mode or a second mode, transmit, if it is determined to operate in the first mode, and prior to exposure of imaging elements to radiation that is to be converted to and captured as image data, a pulse to the imaging elements in order to read an image frame from the imaging elements, the pulse being transmitted so that the image frame is read and the imaging elements become ready to capture image data associated with the radiation substantially immediately before the imaging elements are exposed to the radiation, and transmit a second pulse to the imaging elements in order to read a second image frame from the imaging elements, wherein the second pulse is transmitted at a predetermined time after the exposure of the imaging elements to the radiation is complete According to this aspect, if it is determined to operate in the second mode, then embodiments of the invention operate to transmit, prior to exposure of imaging elements to radiation to be converted to and captured as image data, a third pulse to the imaging elements in order to read a third image frame from the imaging elements, the third pulse being transmitted so that the third image frame is read and the imaging elements become ready to capture image data associated with the radiation substantially immediately before the imaging elements are exposed to the radiation, detect a linear accelerator pulse, determine if the linear accelerator pulse is detected while the third image frame is being read from the imaging elements, transmit, if it is determined that the linear accelerator pulse is not detected while the third image frame is being read from the imaging elements, a fourth pulse to the imaging elements in order to read a fourth image frame from the imaging elements, determine that the exposure of the imaging elements to the radiation is complete, and transmit a fifth pulse to the imaging elements in order to read a fifth image frame from the imaging elements after an immediately-previous image frame is read from the imaging elements.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person skilled in the art to make and use the invention and sets forth the best mode contemplated by the inventor for carrying out the invention. Various modifications, however, will remain readily apparent to those in the art.

Figure 1:
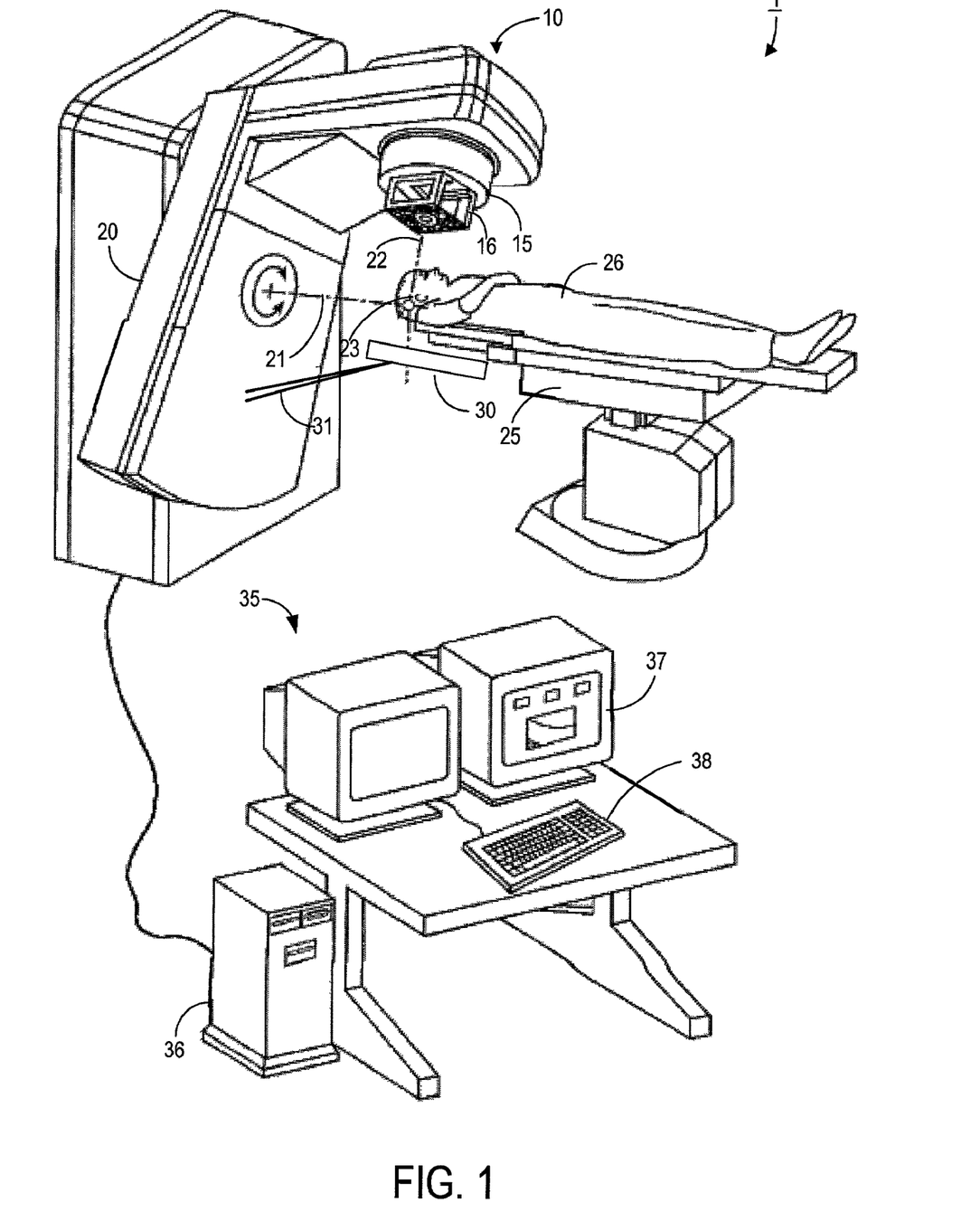
FIG. 1 is diagram illustrating a radiation treatment room according to some embodiments of the present invention.

FIG. 7 illustrates radiation therapy station 1 pursuant to embodiments of the present invention. According to one embodiment of the present invention, radiation therapy station 1 includes linear accelerator (linac) 10, treatment table 25, imaging device 30 and operator station 35. The elements of radiation therapy station 1 are used to deliver radiation to a patient according to a radiation treatment plan.

Linac 10 delivers radiation to a treatment area and is primarily composed of treatment head 15 and gantry 20. Treatment head 15 includes a beam-emitting device (not shown) for emitting a radiation beam and a beam-shielding device, or collimator (not shown) for shaping the beam and for shielding sensitive surfaces from the beam. The beam may comprise electron, photon or any other type of detectable radiation. Accessory tray 16 is mounted on treatment head 15 and may be configured to receive and securely hold attachments used during the course of treatment planning and treatment (such as, for example, reticles, wedges, or the like).

Treatment head 15 is fastened to a projection of gantry 20. Gantry 20 is rotatable around axis 21 before, during and after radiation treatment. During such treatment, radiation from linac 10 is delivered to the beam-emitting device of treatment head 15 and emitted therefrom along beam path 22. Isocenter 23 is located at the intersection of beam path 22 and axis 21. In this regard, isocenter 23 designates a point on which the emitted beam is focused.

Table 25 supports patient 26 during radiation treatment. Table 25 is adjustable to ensure, along with rotation of gantry 20, that an area of patient 26 to be treated is positioned at isocenter 23.

Imaging device 30 is used to perform portal imaging for radiation therapy treatments. More particularly, imaging device 30 is used to acquire images of an internal portion of patient 26 for verification and recordation of a treatment field. These images can be acquired before or after treatment to ascertain that the patient position, as well as the beam shape, conform to a desired treatment plan.

Since the acquired images are used to determine conformance with a treatment plan, accuracy of the images is crucial. Cure rates for many tumors are a sensitive function of the radiation dose they receive, so treatment plans are designed to maximize radiation delivered to a target while minimizing radiation delivered to healthy tissue and organs that often lie in the beam path. Modern treatment plans using Intensity-Modulated RadioTherapy (IMRT), Conformal Radiation Therapy (CRT) and/or composite radiation beam distributions require fine control of beam shape and patient positioning in order to achieve these goals. Accordingly, errors in positioning the patient or in the beam shape that result from poor imaging can cause the delivery of low radiation doses to tumors and high radiation doses to sensitive healthy tissue. The potential for misdelivery increases with increased imaging errors.

In some embodiments, imaging device 30 is a flat-panel imaging device using solid-state amorphous silicon sensors deployed in a two-dimensional array. Other types of imaging devices may be used as imaging device 30. The RID1640, offered by PerkinElmer®, Inc. of Fremont, Calif., is one suitable device. As described in the Background, the sensors record the intensity of received light as stored electrical charge, and may be read to capture an image frame. The captured image frames are then corrected to create an image of the radiation field, thereby allowing quick and efficient verification of the treatment field including patient anatomy, patient position and beam shape. Further details of the structure and operation of imaging device 30 according to some embodiments of the invention are set forth below with respect to FIG. 2 and FIG. 3.

Imaging device 30 may be attached to gantry 20 in any manner, including via extendible and retractable arm structure 31. Pursuant to some embodiments of the present invention, arm structure 31 may be used to advance and retract imaging device 30 to and from an imaging position along beam path 22 in order to acquire portal images required for treatment.

Operator station 35 includes a processor 36 in communication with an operator console 37 (including one or more visual display units or monitor) and an input device such as keyboard 38. Operator station 35 is typically operated by an operator who administers actual delivery of radiation treatment as prescribed by an oncologist. The operator uses keyboard 38 to input data defining a radiation dose to be delivered to the patient, for example, according to the prescription of the oncologist. The data may also be input via another input device, such as a data storage device. Operator console 37 displays data to the operator before during and after the treatment.

Operator station 35 is typically located apart from linac 10, such as in a different room, in order to protect the operator from radiation. For example, linac 10 may be located in a heavily shielded room, such as a concrete vault, which shields the operator from dangerous radiation generated by linac 10.

Processor 36 may include a hardware card (not shown) according to some embodiments of the present invention. The hardware card may include hardware elements such as integrated circuits (ICs), discrete devices, or the like and may also incorporate software such as process steps stored in a programmable memory device. Specifically, such a hardware card may include hardware elements to transmit, prior to exposure of imaging elements to radiation that is to be converted to and captured as image data, a pulse to the imaging elements in order to read an image frame from the imaging elements, wherein the pulse is transmitted so that the image frame is read and the imaging elements become ready to capture image data associated with the radiation substantially immediately before the imaging elements are exposed to the radiation. Additionally, the hardware card may cause transmission of a second pulse to the imaging elements in order to read a second image frame from the imaging elements, wherein the second pulse is transmitted at a predetermined time after the exposure of the imaging elements to the radiation is complete, wherein one of the imaging elements produces second radiation after the exposure of the imaging elements to the radiation is complete, and wherein the predetermined time is a time suitable to substantially capture image data associated with the second radiation.

In some embodiments, the card operates to transmit a pulse as described above and to detect a linear accelerator pulse, determine if the linear-accelerator pulse is detected while the image frame is being read from the imaging elements, transmit, if it is determined that the linear accelerator pulse is not detected while the image frame is being read from the imaging elements, a second pulse to the imaging elements in order to read a second image frame from the imaging elements, determine that the exposure of the imaging elements to the radiation is complete, and transmit a third pulse to the imaging elements in order to read a third image frame from the imaging elements after an immediately-previous image frame is read from the imaging elements.

Such a hardware card may also be installed within linac 10, imaging device 30, or another device in direct or indirect communication with imaging device 30. Process steps according to some embodiments of the invention may also be embodied, in whole or in part, by a software application executed by devices including but not limited to processor 36, linac 10, and/or imaging device 30. Moreover, embodiments of the invention may be embodied by a standalone device connected between linac 10 and operator station 35, between linac 10 and imaging device 30, or elsewhere.

Of course, each of the devices shown in FIG. 1 may include less or more elements than those shown. Moreover, transformation and storage of acquired data may be performed by any one or more of the devices. In addition, embodiments of the invention are not limited to the devices shown in the figure.

Figure 2:
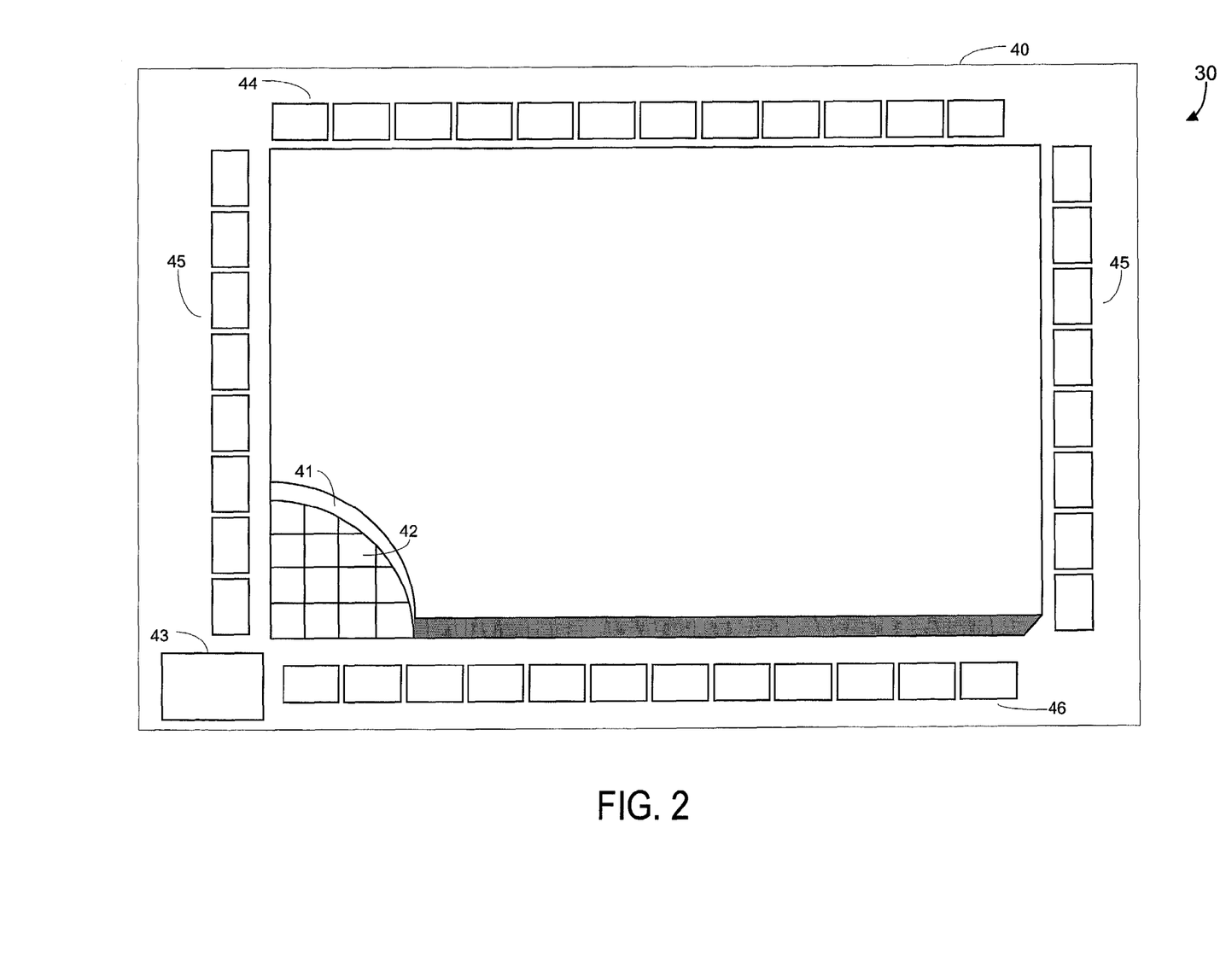
FIG. 2 is an illustration of an imaging device according to some embodiments of the present invention.

FIG. 2 is an illustration of imaging device 30 according to some embodiments of the invention. As shown, imaging device 30 consists of circuit board 40 on which various elements are mounted. One element is scintillator 41, a gadolinium-sulfide layer that absorbs x-ray radiation and emits visible photons having an intensity proportional to that of the absorbed x-rays. Imaging device 30 of FIG. 2 therefore employs indirect detection to create image data from x-rays, as described above. Other types of scintillators usable for indirect detection include Cesium-iodide or Lanex™ fast scintillators. For illustrative purposes, a portion of scintillator 41 is cut away to show imaging elements 42.

Imaging elements 42 comprise a matrix of amorphous silicon photodiodes and associated thin-film transistors. The matrix extends below the area of scintillator 41 shown in FIG. 2. In the case of the RID1640 imaging device mentioned above, 1,048,576 photodiodes are arranged in a 1024×1024 pixels array on 400 μm centers. The resulting photoactive region is approximately 41×41 $cm^2$.

Briefly, the photodiodes of imaging elements 42 absorb visible photons generated by scintillator 41 and the absorbed photons generate a current that is integrated into the photodiodes' self-capacitance as an electrical charge. In this regard, it should be noted that scintillator 41 may also be considered an imaging element according to embodiments of the invention. The electrical charge stored in a photodiode is therefore proportional to an intensity of x-rays absorbed by a portion of scintillator 41 that lies above the photodiode, and can be considered captured image data. The charge is read from the photodiode by applying a signal to a transistor associated with the photodiode and the read charge may be used to construct an image. The arrangement and operation of imaging elements 42 will be described in more detail with respect to FIG. 3.

Timing and control IC 43 controls operation of imaging device 30 in accordance with process steps stored therein and commands received from remotely connected devices such as linac 10 or processor 36. For example, timing and control IC 43 may control bias ICs 44 to apply required bias voltages to the photodiodes of imaging elements 42. Timing and control IC 43 may also control the application of signals to appropriate ones of line driver ICs 45 to initiate reading the amount of charge, or image data, captured in one or more photodiodes of imaging elements 42. Data and signal amplification ICs 46 are then controlled to receive and amplify the image data, which is thereafter multiplexed and converted to digital by timing and control IC 43.

Commands and data can be transmitted to and from imaging device 30 via I/O lines (not shown). Moreover, the elements of imaging device 30 shown in FIG. 2 may be encased in a suitable protective housing.

Figure 3:
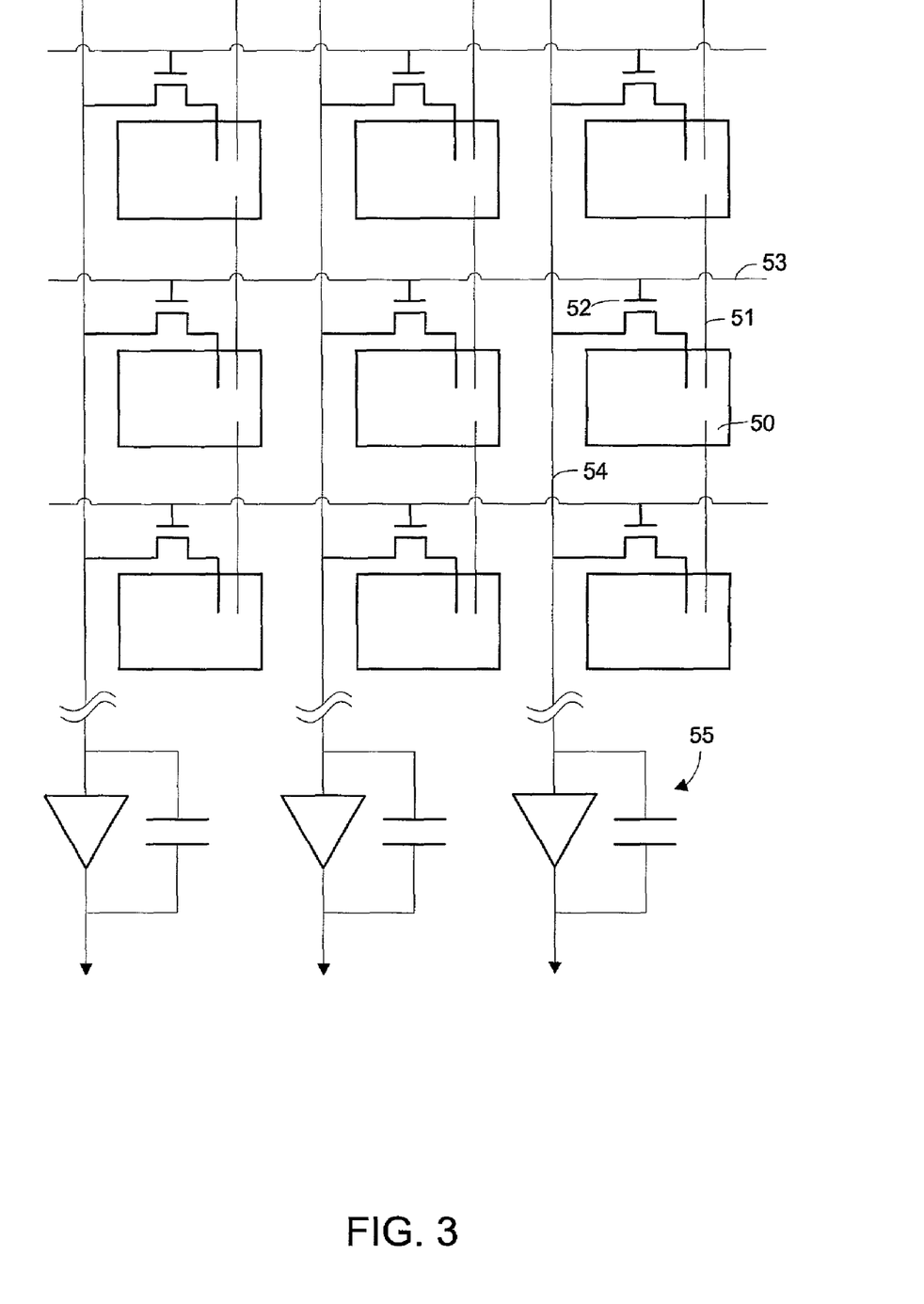
FIG. 3 is a circuit diagram of imaging elements according to some embodiments of the present invention.

FIG. 3 is a circuit diagram of a portion of an array of imaging elements 42 according to some embodiments of the invention. Included in the array are photodiodes 50, which in the present example are based on amorphous silicon and capable of storing electrical charge if exposed to radiation, in this case visible light. Connected to each photodiode 50 is bias line 51, which carries a bias voltage from bias IC 44 that is required to operate the type of photodiodes described herein. Of course, photodiodes or photoconductors other than those described herein may be used in conjunction with some embodiments of the invention.

One thin-film transistor 52 is associated with each photodiode 50. In operation, line driver ICs 45 transmit a pulse over selected ones of control lines 53, thereby energizing the base terminals of thin-film transistors 52 that are connected to the selected control lines. As a result, photodiodes 50 that are associated with the energized transistors 52 discharge over an associated data line 54. The data is amplified by an associated amplifier 55 that is provided by an appropriate data and signal amplification IC 46.

Therefore, in order to read image data captured by a particular photodiode 50, a pulse is transmitted over a control line 53 associated with the particular photodiode 50 and data is read from a data line 54 associated with the particular photodiode 50. In order to read an entire image frame from imaging elements 42, timing and control IC 43 controls line driver ICs 45 and data and signal amplification ICs 46 to read the image data captured by each photodiode 50 of imaging device 30. In this regard, an image frame is read from imaging elements 42 in response to a control pulse received by imaging device 30.

Figure 4:
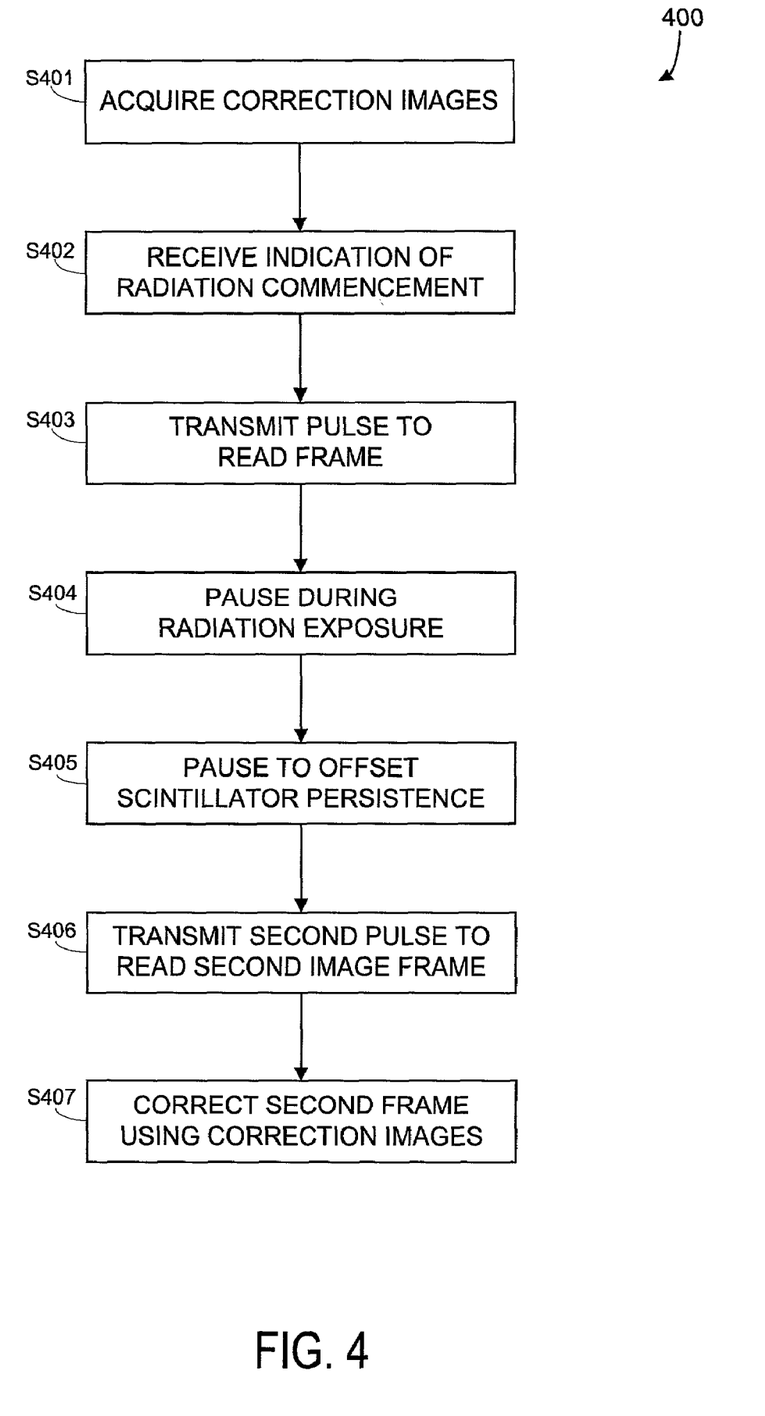
FIG. 4 is a flow diagram illustrating process steps according to some embodiments of the present invention.

FIG. 4 is a flow diagram of process steps 400 according to some embodiments of the invention. Process steps 400, as well as process steps 500 of FIG. 5, may be embodied in a hardware card installed within processor 36, linac 10, imaging device 30, or another device in direct or indirect communication with imaging device 30. Process steps 400 and/or 500 may also be embodied, in whole or in part, by software executed by devices including but not limited to processor 36, linac 10, and/or imaging device 30. Moreover, process steps 400 and/or 500 may be embodied by a standalone device connected between linac 10 and operator station 35, between linac 10 and imaging device 30, or elsewhere.

Briefly, process steps 400 comprise steps to transmit, prior to exposure of imaging elements to radiation that is to be converted to and captured as image data, a pulse to the imaging elements in order to read an image frame from the imaging elements, wherein the pulse is transmitted so that the image frame is read and the imaging elements become ready to capture image data associated with the radiation substantially immediately before the imaging elements are exposed to the radiation. Process steps 400 also include transmission of a second pulse to the imaging elements in order to read a second image frame from the imaging elements, wherein the second pulse is transmitted at a predetermined time after the exposure of the imaging elements to the radiation is complete. Moreover, in some embodiments of process steps 400, one of the imaging elements produces second radiation after the exposure of the imaging elements to the radiation is complete, and the predetermined time is a time suitable to substantially capture image data associated with the second radiation.

Process steps 400 begin at step S401, wherein correction images are acquired. The correction images may be acquired anytime before radiation treatment, but are commonly obtained in the early morning prior to the administration of several radiation treatments throughout the day. In some embodiments, the correction images include images used for offset correction, gain correction, and dead pixel correction.

As described in the Background, an offset image is used to perform offset correction on image frames reflecting image data captured during irradiation. The offset image may be calculated from image frames that were acquired at a same frame rate as to be used during actual radiation treatment. For purposes of the present example, a frame rate of 340 ms will be used during radiation treatment, so the offset image is calculated based on image frames reflecting a 340 ms frame rate. Of course, any suitable frame rate may be used in conjunction with the present invention.

A gain correction image is used to correct for differences in sensitivity and gain among photodiodes 50. A gain correction image is obtained by irradiating imaging device 30 while no object lies between the radiation source and imaging device 30. The gain correction image is also used to identify non-functioning pixels of imaging device 30, or "dead" pixels. An image, or map, is generated based on the identified dead pixels and the map is used to reassign the value of each dead pixel to a value that is based on values of neighboring pixels.

An indication that radiation is to commence is received in step S402. In this regard, patient 26 may be positioned prior to step S402 so that a treatment area of patient 26 is located at isocenter 23. The indication may be received directly or indirectly from linac 10, from processor 36, or from another device that is capable of determining that radiation is to commence. In some embodiments, the indication is embodied in a reset pulse sent from linac 10. Next, in step S403, a pulse is transmitted in order to read image data from imaging elements 42 of imaging device 30.

The pulse may be transmitted directly or indirectly to imaging device 30, and may be received by an I/O line of imaging device 30. In response, timing and control IC 43 issues a control pulse in order to read image data of an image frame from imaging elements 42. In some embodiments, the pulse transmitted in step S403 is the control pulse. Since imaging device 30 has not yet been exposed to radiation, the resulting image frame will only show effects of dark current and will not be a portal image. The image may therefore be discarded.

According to some embodiments, the pulse of step S403 is timed so that the image frame is read and imaging elements 42 become ready to capture image data associated with radiation substantially immediately before imaging elements 42 are exposed to the radiation. For example, if it is known that linac 10 transmits a reset pulse 600 ms prior to delivering radiation and a time required to read an image frame is 350 ms, the pulse of step S403 might be transmitted 225 ms after receipt of the reset pulse, or 375 ms before the delivery of radiation. Therefore, a time period between reading the image frame and the start of radiation is 25 ms. In some embodiments, dark current effects may be reduced by timing the pulse of step S403 so as to reduce this time period.

Also in some embodiments, more than one pulse is transmitted in step S403. The last of these pulses is transmitted so that a corresponding image frame is read and imaging elements 42 become ready to capture image data associated with radiation substantially immediately before imaging elements 42 are exposed to the radiation. Pulses transmitted prior to the last pulse may serve to remove more dark current effects than would be removed if only one pulse was sent in step S403. Of course, a delay between transmission of the reset pulse by linac 10 and a start of radiation should be long enough to allow the reading of frames associated with each of the pulses transmitted in step S403. For example, in a case of a 1000 ms delay between transmission of the reset pulse and a start of radiation and a frame read time of 350 ms, two pulses may be sent in step S403.

Process steps S404 pause at step S404 while linac 10 exposes isocenter 23 and imaging device 30 to radiation according to a treatment plan. After exposure is complete, flow proceeds to step S405. Completion of the exposure may be determined by means of a "radiation on" signal received from Linac 10. In particular, the "radiation on" signal is active while linac 10 delivers radiation and is inactive when delivery is complete.

Flow pauses again at step S405 in order to allow photodiodes 50 to absorb light generated by scintillator 41 after radiation is complete. In this regard, a slight delay exists between reception of radiation by scintillator 41 and the complete generation of visible photon radiation proportional to the intensity of the received radiation. This delay is caused by a characteristic of scintillator 41 known as persistence. The pause of step S405 is therefore intended to substantially capture image data associated with all visible photons generated by scintillator 41 in response to the received x-ray radiation. The period of the step S405 pause may differ among imaging devices, but a period of 1.5 ms has been found to be satisfactory using the RID1640 imaging device. Step S405 may be omitted in some embodiments using imaging devices that do not present a persistence effect.

Next, a second pulse is transmitted in order to read a second image frame from imaging elements 42 of imaging device 30. The second image frame represents visible light incident to imaging device 30 during a time period since a last image frame was read therefrom. The second image frame is then stored and corrected in step S407 using the correction images acquired in step S401.

Process steps 400 cause photodiodes 50 of imaging device 30 to store image data produced over the course of an entire dose of radiation. This feature has been shown in some embodiments to improve a signal-to-noise ratio of the resulting image and/or to reduce artifacts caused by pulsing characteristics of linac 10. This feature may also make process steps 400 more suitable for low radiation doses (<4 cGy) because at higher doses and/or increases in the length of the step S404 pause, photodiodes 50 may saturate and be unable to hold an amount of electrical charge representative of the incident light generated by the radiation.

The suitability of process steps 400 may therefore depend on the dosage and/or type of imaging device used. Embodiments of process steps 500 of FIG. 5, on the other hand, may be more suited for use in conjunction with high and/or low radiation doses.

Figure 5:
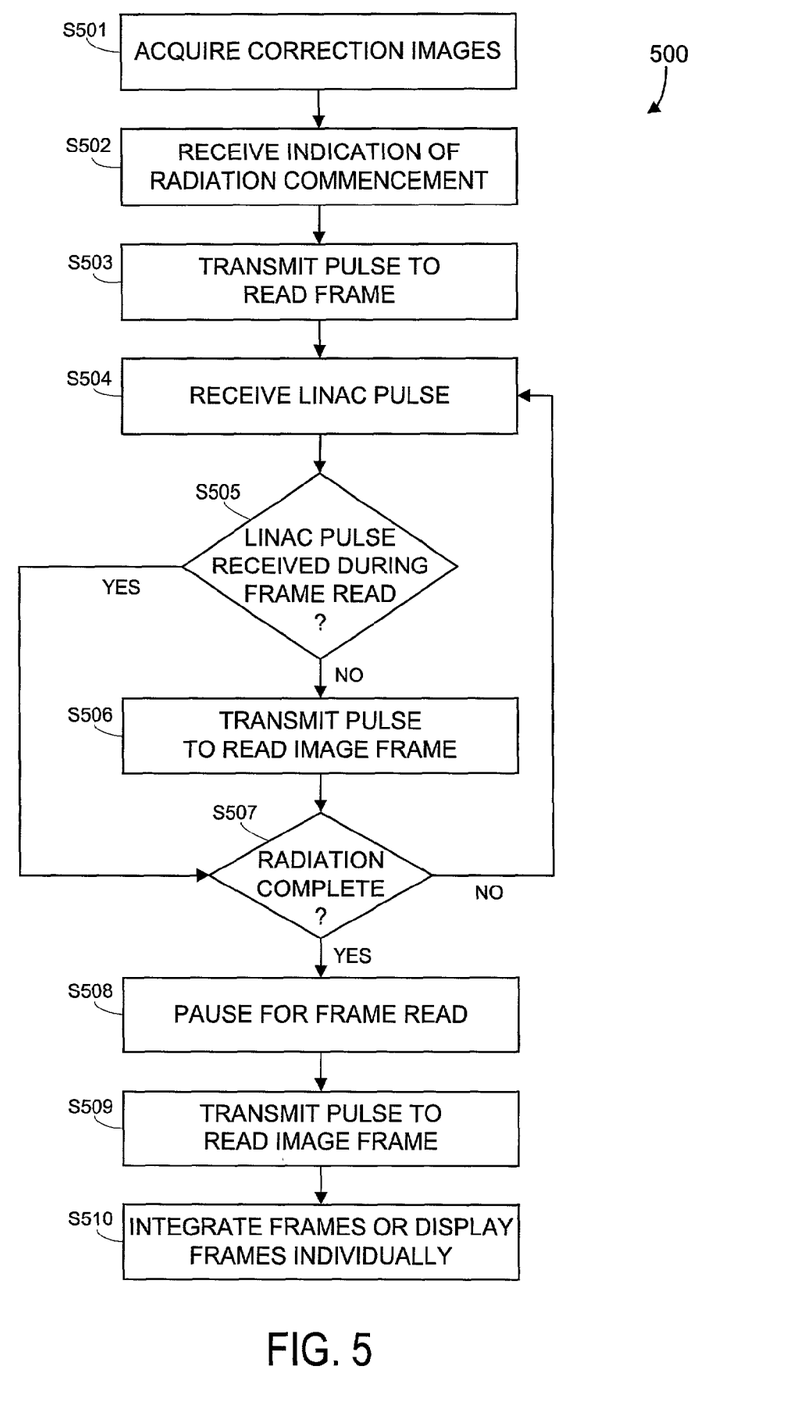
FIG. 5 is a flow diagram illustrating process steps according to some embodiments of the present invention.

Generally, process steps 500 provide transmission, prior to exposure of imaging elements to radiation to be converted to and captured as image data, of a pulse to the imaging elements in order to read an image frame from the imaging elements, the pulse being transmitted so that the image frame is read and the imaging elements become ready to capture image data associated with the radiation substantially immediately before the imaging elements are exposed to the radiation, detection of a linear accelerator pulse, determination of whether the linear accelerator pulse is detected while the image frame is being read from the imaging elements, transmission of a second pulse to the imaging elements in order to read a second image frame from the imaging elements if it is determined that the linear accelerator pulse is not detected while the image frame is being read from the imaging elements, determination that the exposure of the imaging elements to the radiation is complete, and transmission of a third pulse to the imaging elements in order to read a third image frame from the imaging elements after an immediately-previous image frame is read from the imaging elements.

Steps S501 through S503 may proceed similarly to step S401 through S403 of process steps 400, and therefore will not be presently described. In step S504, a pulse is received from linac 10. The pulse is a signal periodically sent from linac 10 during radiation treatment. In some embodiments, the linac pulse differs from the "radiation on" signal described above. It is then determined in step S505 whether the linac pulse was received while an image frame was being read from imaging elements 42.

According to some embodiments, reading of an image frame in response to the step S503 pulse is completed before step S504, because the pulse is timed so that the frame is read before radiation treatment begins. Therefore, upon first encountering step S505, flow continues to step S506, wherein a pulse is transmitted to read an image frame from imaging elements 42. In some embodiments, the read image frame is stored and corrected using the correction images obtained in step S501. Next, in step S507, it is determined whether radiation treatment is complete, perhaps by means of the "radiation on" signal mentioned above. If the treatment is not complete, flow returns to step S504 for receipt of another pulse from linac 10.

If it is determined in step S505 that the pulse was received in step S504 during the reading of an image frame, flow continues to step S507 as described above. Accordingly, image frames are read in response to received linac pulses, but linac pulses received during a frame reading that was triggered by a previous linac pulse are not used for such triggering.

Once it is determined in step S507 that radiation treatment is complete, flow pauses at step S508 to allow completion of a frame reading that may be in progress. Accordingly, the pause length may be set in view of the time it takes for a frame to be read from imaging elements 42. In some embodiments, the step S508 pause is set to 340 ms for a frame read time of 340 ms.

Next, in step S509, a pulse is transmitted to control lines 53 of imaging device 30 in order to read an image frame therefrom. This last image frame integrates image data acquired and stored between the end of a last frame read and the completion of radiation delivery. As specified above, some embodiments provide storage and correction of the frame after reading thereof. In step S510, the frames read in steps S506 and S509 and subsequently corrected are integrated to produce a final image. Alternatively, the frames can be individually displayed to create a moving image usable to verify each segment of IMRT.

It should be noted that a single system composed of one or more hardware devices and/or software elements may be used to implement both the FIG. 4 and the FIG. 5 process steps. Generally, some embodiments of such a system include an initial determination of whether to operate according to a mode reflecting process steps 400 or according to a mode reflecting process steps 500. Depending on the determination, either process steps 400 or process steps 500 are performed. The determination may be based on one or more of a dose amount, a desired accuracy, and characteristics of imaging device 30 such as a saturation point of photodiodes 50. In some embodiments, process steps 400 are performed for doses less than 4 cGy and process steps 500 are performed for doses equal to or greater than 4 cGy.

Figure 6:
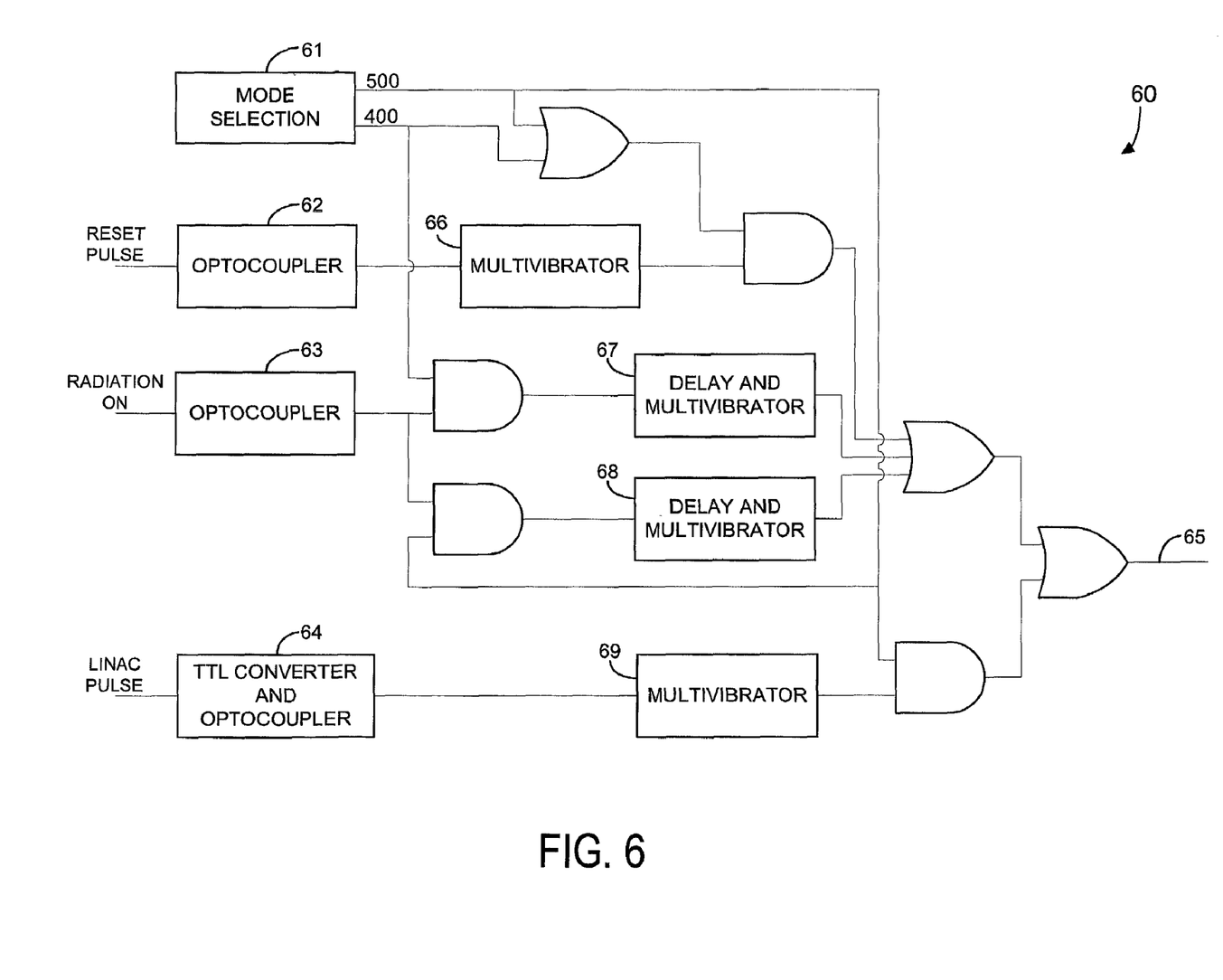
FIG. 6 is a functional logic diagram of a device for executing the FIG. 4 and FIG. 5 process steps according to some embodiments of the present invention.

FIG. 6 shows a functional logic diagram of circuit 60 for implementing process steps 400 and 500 according to some embodiments of the invention. Particularly, output line "500" of mode selection element 61 goes active if the mode reflected by process steps 500 is selected, while output line "400" goes active if the mode reflected by process steps 400 is selected. As described above, the mode selected may be based on many factors, and may be input to mode selection element 61 via a control line, switch, or the like.

Optocouplers 62 and 63 receive signals from linac 10 and electrically isolate linac 10 from circuit 60. The received signals are, respectively, a reset pulse received in steps S402 and S502 and a "radiation on" signal detected in steps S404 and S507. TTL converter and optocoupler 64 receives the linac pulse of step S504 and also isolates linac 10 from circuit 60. Accordingly, circuit 60 uses inputs from mode selection element 61 and a reset pulse, "radiation on" signal and linac pulse from linac 10 to produce a trigger signal on trigger output 65 that causes an image frame to be read from imaging elements 42 of imaging device 30.

In this regard, monostable multivibrator 66 produces the pulse transmitted in steps S403 and S503 in response to a reset pulse received from linac 10. In some embodiments, multivibrator 66 is activated by a rising edge of the reset pulse. Delay and monostable multivibrator 67 is activated by a falling edge of the "radiation on" signal during process steps 400. As a result, delay and multivibrator 67 produces a pulse on trigger output 65 at a specified time after the "radiation on" signal goes inactive. In the embodiment described above, the specified time is 1.5 ms.

Delay and multivibrator 67 is inactive in a case that process steps 500 are being performed. In this case, delay and monostable multivibrator 68 produces a pulse on trigger output 65 at a specified delay after a falling edge of the "radiation on" signal. This pulse is transmitted in step S509, and the specified delay according to the above-described embodiment is 340 ms.

Monostable multivibrator 69 produces pulses on trigger output 65 in response to a received linac pulse. As described above with respect to some embodiments of process steps 500, the produced pulses are ignored if they are transmitted while a frame is being read.

Figure 7:
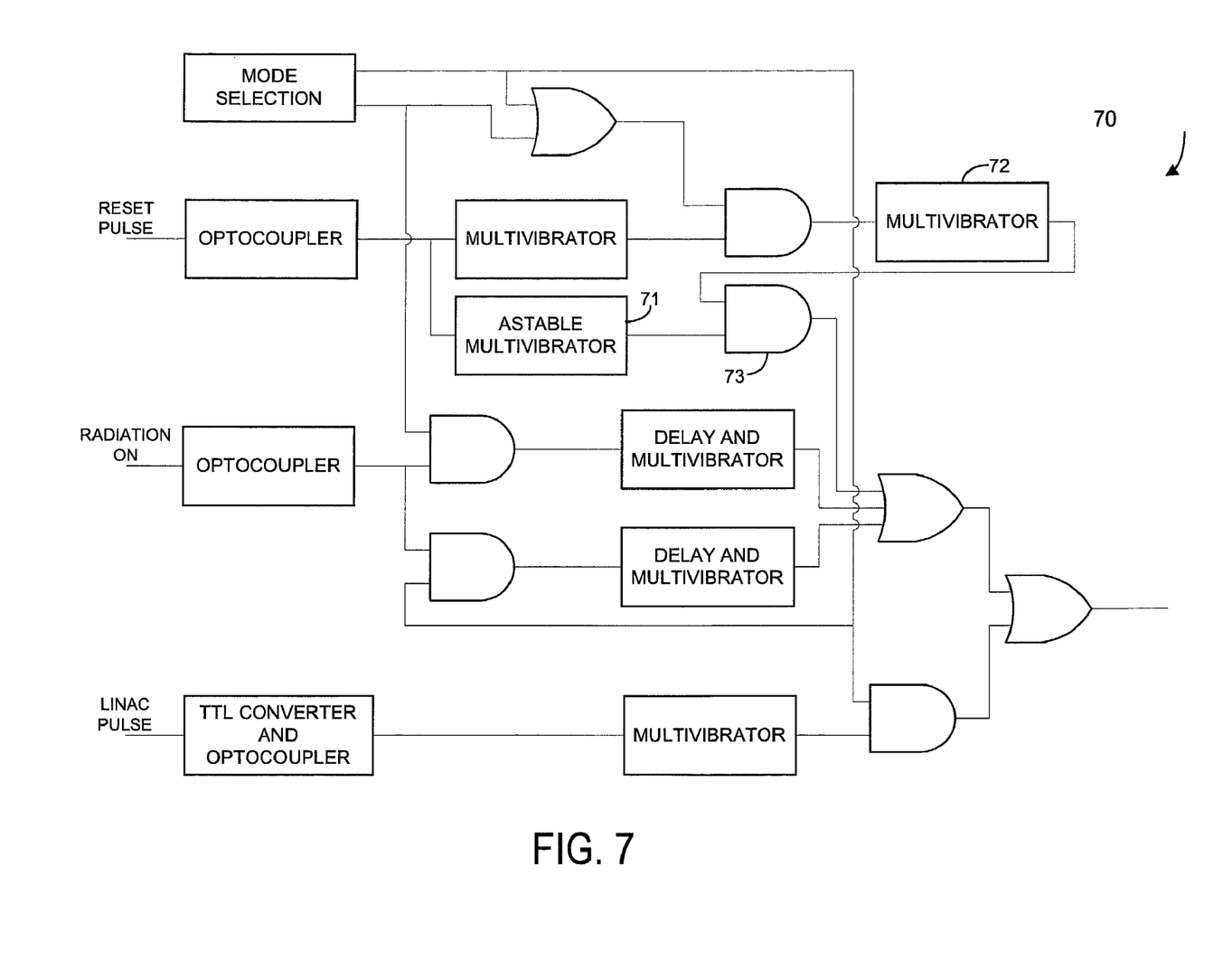
FIG. 7 is a functional logic diagram of a device for executing the FIG. 4 and FIG. 5 process steps according to some embodiments of the present invention.

FIG. 7 illustrates a functional logic diagram of circuit 70 according to some embodiments of the invention. Circuit 70 includes components identical to those shown in FIG. 6 and also includes astable multivibrator 71, monostable multivibrator 72, and AND gate 73. These additional elements operate to transmit multiple pulses to read out an image frame after receipt of a reset pulse from linac 10 and before receipt of the "radiation on" signal. Using the frame read time of the previous examples, astable multivibrator 71 may be set to transmit a pulse every 345 ms.

Circuit 60 or circuit 70 may be embodied as standard hardware or on an installed hardware card in one or more of a standalone device, linac 10, imaging device 30, processor 36, or another device. Of course, functions of circuit 60 and/or circuit 70 may also be provided by software or combinations of software and hardware.

Those in the art will appreciate that various adaptations and modifications of the above-described embodiments can be configured without departing from the scope and spirit of the invention. Also, embodiments of the present invention may differ from the description of process steps 400 and/or 500. In addition, the particular arrangement of the process steps is not meant to imply a fixed order to the steps; embodiments of the present invention can be practiced in any order that is practicable. Therefore, it is to be understood that, within the scope of the appended claims, the invention may be practiced other than as specifically described herein.

What is claimed is:

1. A method comprising:
   transmitting an electrical pulse while not transmitting radiation to imaging elements in order to initiate reading a first image frame from the imaging elements;
   reading the first image frame from the imaging elements;
   exposing the imaging elements to radiation emitted from a linear accelerator substantially immediately after the first image frame is read;
   detecting a linear accelerator pulse while the imaging elements are exposed to the radiation;
   in response to the linear accelerator pulse, transmitting a second electrical pulse while not transmitting radiation to the imaging elements in order to initiate reading a second image frame from the imaging elements;
   detecting a second linear accelerator pulse while the imaging elements are exposed to the radiation;
   determining that the second linear accelerator pulse was detected while the second image frame is being read from the imaging elements;
   detecting a third linear accelerator pulse while the imaging elements are exposed to the radiation, wherein no electrical pulse is transmitted to the imaging elements to initiate reading an image frame from the imaging elements between the detection of the second linear accelerator pulse and the detection of the third linear accelerator pulse;
   determining that the third linear accelerator pulse was not detected while the second image frame is being read from the imaging elements;
   in response to the determination that the third linear accelerator pulse was not detected while the second image frame is being read, transmitting a third electrical pulse to the imaging elements in order to initiate reading a third image frame from the imaging elements; and
   displaying the second image frame, and the third image frame to an operator.

2. The method according to claim 1,
   wherein the imaging elements comprise a plurality of charge-storing devices, and
   wherein the electrical pulse causes substantial discharge of the plurality of charge-storing devices.

3. The method according to claim 1, further comprising:
   determining that the exposure of the imaging elements to the radiation is complete; and
   transmitting a fourth electrical pulse to the imaging elements in order to read a fourth image frame from the imaging elements after an immediately-previous image frame is read from the imaging elements.

4. A non-transitory computer-readable medium storing processor-executable process steps, the process steps comprising:
   a step to transmit an electrical pulse while not transmitting radiation to imaging elements in order to initiate reading a first image frame from the imaging elements;
   a step to read the first image frame from the imaging elements;
   a step to expose the imaging elements to radiation emitted from a linear accelerator substantially immediately after the first image frame is read;
   a step to detect a linear accelerator pulse while the imaging elements are exposed to the radiation;
   a step to transmit, in response to the linear accelerator pulse, a second electrical pulse to the imaging elements while not transmitting radiation in order to initiate reading a second image frame from the imaging elements;
   a step to detect a second linear accelerator pulse while the imaging elements are exposed to the radiation;
   a step to determine that the second linear accelerator pulse was detected while the second image frame is being read from the imaging elements;
   a step to detect a third linear accelerator pulse while the imaging elements are exposed to the radiation, wherein no electrical pulse is transmitted to the imaging elements to initiate reading an image frame from the imaging elements between the detection of the second linear accelerator pulse and the detection of the third linear accelerator pulse;
   a step to determine that the third linear accelerator pulse was not detected while the second image frame is being read from the imaging elements;
   a step to transmit, in response to the determination that the third linear accelerator pulse was not detected while the second image frame is being read, a third electrical pulse to the imaging elements in order to initiate reading a third image frame from the imaging elements; and
   a step to display the second image frame, and the third image frame to an operator.

5. The non-transitory medium according to claim 4,
   wherein the imaging elements comprise a plurality of charge-storing devices, and wherein the electrical pulse substantially discharges the plurality of charge-storing devices.

6. The non-transitory medium according to claim 4, the process steps further comprising:
   a step to determine that the exposure of the imaging elements to the radiation is complete; and
   a step to transmit a fourth electrical pulse to the imaging elements in order to read a fourth image frame from the imaging elements after an immediately-previous image frame is read from the imaging elements.

7. A device comprising:
   a non-transitory memory storing processor-executable process steps;
   a processor in communication with the memory and operative in conjunction with the stored process steps to:
   transmit an electrical pulse while not transmitting radiation to imaging elements in order to initiate reading of a first image frame from the imaging elements;
   read the first image frame from the imaging elements;
   expose the imaging elements to radiation emitted from a linear accelerator substantially immediately after the first image frame is read;
   detect a linear accelerator pulse while the imaging elements are exposed to the radiation;
   transmit, in response to the linear accelerator pulse, a second electrical pulse while not transmitting radiation to the imaging elements in order to initiate reading a second image frame from the imaging elements;
   detect a second linear accelerator pulse while the imaging elements are exposed to the radiation;
   determine that the second linear accelerator pulse was detected while the second image frame is being read from the imaging elements;
   detect a third linear accelerator pulse while the imaging elements are exposed to the radiation, wherein no electrical pulse is transmitted to the imaging elements to initiate reading an image frame from the imaging elements between the detection of the second linear accelerator pulse and the detection of the third linear accelerator pulse;
   determine that the third linear accelerator pulse was not detected while the second image frame is being read from the imaging elements;
   transmit, in response to the determination that the third linear accelerator pulse was not detected while the second image frame is being read, a third electrical pulse to the imaging elements in order to initiate reading a third image frame from the imaging elements; and
   display the second image frame, and the third image frame to an operator.

8. The device according to claim 7,
   wherein the imaging elements comprise a plurality of charge-storing devices, and
   wherein the electrical pulse substantially discharges the plurality of charge-storing devices.

9. The device according to claim 7, the processor further operative in conjunction with the stored process steps to:
   determine that the exposure of the imaging elements to the radiation is complete; and
   transmit a fourth electrical pulse to the imaging elements in order to read a fourth image frame from the imaging elements after an immediately-previous image frame is read from the imaging elements.

* * * * *